United States Patent [19]

Lichtner, Jr.

[11] Patent Number: 5,928,995
[45] Date of Patent: Jul. 27, 1999

[54] HERBICIDAL MIXTURES

[75] Inventor: Francis Thomas Lichtner, Jr., Newark, Del.

[73] Assignee: E. I. du Pont de Nemours and Company, Wilmington, Del.

[21] Appl. No.: 08/945,865

[22] PCT Filed: Apr. 29, 1996

[86] PCT No.: PCT/US96/05951

§ 371 Date: Nov. 3, 1997

§ 102(e) Date: Nov. 3, 1997

[87] PCT Pub. No.: WO96/34528

PCT Pub. Date: Nov. 7, 1996

[30] Foreign Application Priority Data

May 5, 1995 [FR] France .................................. 95 05431

[51] Int. Cl.⁶ ............................ A01N 57/00; A01N 43/64
[52] U.S. Cl. ............................ 504/128; 504/127; 504/133
[58] Field of Search .................................. 504/128, 127, 504/133

[56] References Cited

U.S. PATENT DOCUMENTS

| 4,315,765 | 2/1982 | Large ............................ 71/87 |
|---|---|---|
| 4,405,531 | 9/1983 | Franz ............................ 260/501.12 |
| 4,940,835 | 7/1990 | Shah et al. ............................ 800/205 |
| 4,971,908 | 11/1990 | Kishore et al. ............................ 435/172.1 |
| 5,090,993 | 2/1992 | Moon ............................ 71/93 |
| 5,188,642 | 2/1993 | Shah et al. ............................ 47/58 |
| 5,310,667 | 5/1994 | Eichholtz et al. ............................ 435/172.3 |

FOREIGN PATENT DOCUMENTS

| 0 318 276 | 5/1989 | European Pat. Off. |
|---|---|---|
| 0 336 587 | 10/1989 | European Pat. Off. |
| 2 169 806 | 7/1986 | United Kingdom . |
| WO 89/04607 | 6/1989 | WIPO . |
| WO 92/00377 | 1/1992 | WIPO . |
| WO 92/04449 | 3/1992 | WIPO . |
| WO 92/06201 | 4/1992 | WIPO . |
| WO 92/08353 | 5/1992 | WIPO . |
| WO 92/19719 | 11/1992 | WIPO . |
| WO 93/25081 | 12/1993 | WIPO . |

OTHER PUBLICATIONS

Hance et al., *Weed Control Handbook*, 8ᵗʰ Ed., 1989.

*Primary Examiner*—Allen J. Robinson

[57] ABSTRACT

This invention relates to herbicidal mixtures of triflusulfuron methyl and glyphosate, herbicidal compositions of said mixtures, and a method for the use of said mixtures to control undesired vegetation.

11 Claims, No Drawings

HERBICIDAL MIXTURES

This application is a 371 of PCT/US96/05951 filed Apr. 29, 1996.

FIELD OF THE INVENTION

The present invention relates to mixtures of herbicides that have a synergistic effect on weeds and which are safe to crop plants.

BACKGROUND OF THE INVENTION

The control of undesired vegetation is extremely important in achieving high crop efficiency. Achievement of selective control of the growth of weeds especially in such useful crops as rice, soybeans, sugar beets, corn, potatoes, wheat, barley, tomatoes and plantation crops among others is very desirable. Unchecked weed growth in such useful crops can cause significant reduction in productivity and thereby result in increased costs to the consumers. The control of undesired vegetation in noncrop areas is also important. The need for finding products that achieve such results continues to be commercially important.

U.S. Pat. No. 5,090,993 discloses triflusulfuron methyl and describes its utility for selective weed control in sugar beets. U.S. Pat. Nos. 4,315,765 and 4,405,531 disclose herbicidal salts of glyphosate. WIPO publications WO 92/00377, WO 92/04449, WO 92/06201 and WO 92/19719 and U.S. Pat. Nos. 4,940,835, 4,971,908, 5,188,642 and 5,310,667 disclose methods for genetically transforming sugar beets to make them resistant to glyphosate. None of these references disclose the mixtures of this invention.

SUMMARY OF THE INVENTION

This invention relates to mixtures of methyl 2-[[[[[4-(dimethylamino)-6-(2,2,2-trifluoroethoxy)-1,3,5-triazin-2-yl]amino]carbonyl]amino]sulfonyl]-3-methylbenzoate (triflusulfuron methyl, Formula I)

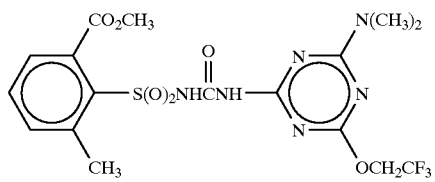

and agriculturally suitable salts thereof with N-(phosphonomethyl)glycine (glyphosate, Formula II)

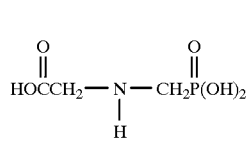

and agriculturally suitable salts, which have now been discovered to synergistically control weeds. This invention also relates to herbicidal compositions comprising effective amounts of the aforesaid mixtures and at least one of the following: surfactant, solid or liquid diluent. This invention also relates to a method for controlling undesired vegetation comprising applying to the locus of the vegetation herbicidally effective amounts of the aforesaid mixtures.

Agriculturally suitable salts of N-(phosphonomethyl)glycine (Formula II) include, but are not limited to, the salts described by Formula IIa

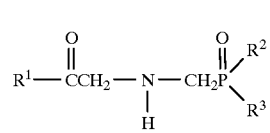

wherein $R^1$, $R^2$ and $R^3$ are independently selected from the group consisting of —OH and —$OR^4$, wherein $R^4$ is a salt-forming cation selected from the group consisting of alkali metals, alkaline earth metals, ammonium, and alkyl amrnmonium and mixtures thereof, provided that no more than two of $R^1$, $R^2$ and $R^3$ are —$OR^4$ when $R^4$ is ammonium or alkyl ammonium and that no more than two of $R^1$, $R^2$ and $R^3$ are —OH; $R^4$ can also be alkyl sulfonium or alkyl sulfoxonium when $R^1$ and $R^3$ are —OH. Alkyl ammonium includes mono-, di-, tri- and tetra-alkylammonium. Alkyl sulfonium means trialkylsulfonium, and alkyl sulfoxonium means trialkylsulfoxonium, where the alkyl groups are independently $C_1$–$C_3$ alkyl.

The mixtures of the invention preferred for enhanced activity include:

1. A herbicidal mixture comprising the sulfonylurea of Formula I and the mono (isopropylammonium) salt of N-(phosphonomethyl)glycine (Formula II) having the common name glyphosate-isopropylammonium.
2. A herbicidal mixture comprising the sulfonylurea of Formula I and the mono (trimethylsulfonium) salt of N-(phosphonomethyl)glycine (Formula II) having the common name glyphosate-trimesium.

For reason of weed control spectrum and/or crop selectivity, the preferred crops for application of the mixtures of this invention are sugar beet lines, varieties and cultivars containing at least one gene that confers tolerance to herbicides containing N-(phosphonomethyl)glycine or an agriculturally suitable salt as the active ingredient.

DETAILS OF THE INVENTION

The Formula I sulfonylurea can be prepared as described in U.S. Pat. No. 5,090,993. The synthesis involves the coupling of the N-silylsulfonamide of Formula 1 with the heterocyclic carbamate of Formula 2.

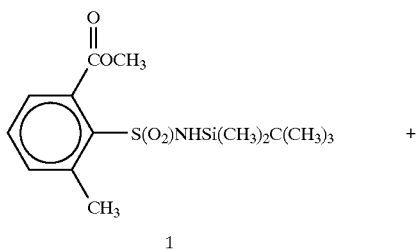

-continued

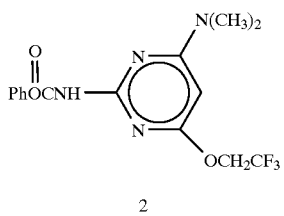

2

→ I

The mixtures of the present invention can include the sulfonylurea of Formula I in the form of agriculturally suitable salts thereof. These can be prepared in a number of ways known in the art. For example, metal salts can be made by contacting the sulfonylurea of Formula I with a solution of an alkali or alkaline earth metal salt having a sufficiently basic anion (e.g., hydroxide, alkoxide, carbonate or hydride). Quaternary amine salts can be made by similar techniques.

Salts of the sulfonylurea of Formula I can also be prepared by exchange of one cation for another. Cationic exchange can be effected by direct contact of an aqueous solution of a salt of the sulfonylurea of Formula I (e.g., alkali or quaternary amine salt) with a solution containing the cation to be exchanged. This method is most effective when the desired salt containing the exchanged cation is insoluble in water and can be separated by filtration.

Exchange may also be effected by passing an aqueous solution of a salt of the sulfonylurea of Formula I (e.g., an alkali metal or quaternary amine salt) through a column packed with a cation-exchange resin containing the cation to be exchanged for that of the original salt and the desired product is eluted from the column. This method is particularly useful when the desired salt is water soluble (e.g., a potassium, sodium or calcium salt).

N-(phosphonomethyl)glycine (Formula II) and its agriculturally suitable salts, including those of Formula IIa, can be prepared by methods described in U.S. Pat. No. 4,315,765 and U.S. Pat. No. 4,405,531.

Formulation/Utility

The mixtures of the Formula I and Formula II (including Formula IIa) compounds can be formulated in a number of ways:

(a) the Formula I and Formula II compounds can be formulated separately and applied separately or applied simultaneously in an appropriate weight ratio, e.g., as a tank mix; or (b) the Formula I and Formula II compounds can be formulated together in the proper weight ratio.

Mixtures of the Formula I and Formula II compounds will generally be used in formulation with an agriculturally suitable carrier comprising a liquid or solid diluent and/or a surfactant wherein the formulation is consistent with the physical properties of the active ingredients, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or watersoluble. Active ingredients can be (micro)encapsulated and further formed into a suspension or solid formulation; alternatively the entire formulation of active ingredient can be encapsulated (or "overcoated"). Encapsulation can control or delay release of the active ingredients. Sprayable formulations can be extended in suitable media and used at spray volumes from about one to several hundred liters per hectare. High-strength compositions are primarily used as intermediates for further formulation.

The formulations will typically contain effective amounts of active ingredients, diluent and surfactant within the following approximate ranges which add up to 100 percent by weight.

|  | Weight Percent | | |
| --- | --- | --- | --- |
|  | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., Handbook of Insecticide Dust Diluents and Carriers, 2nd Ed., Dorland Books, Caldwell, N.J. Typical liquid diluents are described in Marsden, Solvents Guide, 2nd Ed., Interscience, New York, 1950. McCutcheon's Detergents and Emulsifiers Annual, Allured Publ. Corp., Ridgewood, N.J., as well as Sisely and Wood, Encyclopedia of Surface Active Agents, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillinite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Chemically stabilized aqueous sulfonylurea or agriculturally suitable sulfonylurea salt dispersions are taught in U.S. Pat. No. 4,936,900. Solution formulations of sulfonylureas with improved chemical stability are taught in U.S. Pat. No. 4,599,412. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering*, Dec. 4, 1967, pp 147–48, *Perry's Chemical Engineer's Handbook*, 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways.

Example A

High Strength Concentrate

| | |
|---|---|
| triflusulfuron methyl | 4.7% |
| glyphosate-isopropylammonium | 93.8% |
| silica aerogel | 0.5% |
| synthetic amorphous fine silica | 1.0%. |

Example B

Wettable Powder

| | |
|---|---|
| triflusulfuron methyl | 5.0% |
| glyphosate-trimesium | 60.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example C

Granule

| | |
|---|---|
| triflusulfuron methyl | 0.8% |
| glyphosate-isopropylammonium | 9.2% |
| attapulgite granules (low volatile matter, 0.71/0.30 mm; U.S.S. No. 25–50 sieves) | 90.0%. |

Example D

Aqueous Solution Suspension

| | |
|---|---|
| triflusulfuron methyl | 0.1% |
| glyphosate-isopropylammonium | 24.9% |
| hydrated attapulgite | 3.0% |
| crude calcium ligninsulfonate | 10.0% |
| sodium dihydrogen phosphate | 0.5% |
| water | 61.5%. |

Example E

Extruded Pellet

| | |
|---|---|
| triflusulfuron methyl | 0.2% |
| glyphosate-isopropylammonium | 24.8% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

-continued

Example F

Wettable Powder

| | |
|---|---|
| triflusulfuron methyl | 0.1% |
| glyphosate-isopropylammonium | 64.9% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Utility

Test results indicate that mixtures of compounds of Formula I and Formula II (including Formula IIa) are highly active postemergent herbicides, providing unexpected synergistic control of selected grass and broadleaf weeds. Because of the efficacy of the mixtures of the present invention in controlling weeds that commonly infest sugar beet fields, they are particularly valued for their selective tolerance by sugar beet plants containing at least one gene that confers resistance to N-(phosphonomethyl)glycine and its agriculturally suitable salts. Sugar beet varieties, cultivars, and lines that have been "gene-altered" to confer resistance to N-(phosphonomethyl)glycine can be developed by a variety of methods used individually or in combination including: modification to increase biosynthesis of 5-enolpyruvyl-3-phosphoshikimate synthase, incorporation of genes encoding 5-enolpyruvyl-3-phosphoshikimate synthase with structure modified to reduce its inhibition by N-(phosphonomethyl)glycine, and incorporation of genes encoding enzymes to degrade N-phosphonmethylglycine, by methods known in the art, including those described in WO 92/00377, WO 92/04449, WO 92/06201 and WO 92/19719, U.S. Pat. No. 4,940,835, U.S. Pat. No. 4,971,908, U.S. Pat. No. 5,188,642 and U.S. Pat. No. 5,310,667.

In the context of this disclosure, a "line" is a group of plants of similar parentage that display little or no genetic variation between individuals for at least one trait. Such lines may be created by one or more generations of self-pollination and selection, or by vegetative propagation from a single parent, such as by tissue or cell culture techniques. A "variety" or "cultivar" refers to an agronomically superior line that has been extensively tested and is (or was) being used for commercial production.

The Formula I and Formula II mixtures of this invention can additionally be used in combination with other commercial herbicides, insecticides or fungicides. A mixture of one or more additional herbicides with the Formula I and Formula II mixtures of this invention may be particularly useful for weed control. In certain instances, combinations with other herbicides having similar spectrum of control but a different mode of action will be particularly advantageous for resistance management. Examples of other herbicides as mixture partners are: barban, bromoxynil, clodinafop, chloridazon, chlorpropham, cycloate, dalapon, desmedipham, diallate, diethatyl, endothal, EPTC, fenoxaprop, fenoxaprop-P, fluazifop, ethofumesate, glufosinate, haloxyfop, lenacil, metamitron, pebulate, phenmedipham, propham, sethoxydim, TCA, tralkoxydim, trifluralin, and quizalofop.

An herbicidally effective amount of both the compounds of Formula I and Formula II will vary depending on environmental conditions, formulation, method of application, amount and type of vegetation present, etc. The use rate ratios of Formula I to Formula II are in general 1:8 to 1:500, with ratios of 1:15 to 1:100 preferred for most uses. In general, the Formula I compound is applied at a rate from 1 to 30 g ai/ha and Formula II compound is applied at a rate from 125 to 1500 g ai/ha. Preferably, Formula I compound is applied at a rate from 10 to 15 g ai/ha, and the Formula II compound is applied at a rate from 250 to 1000 g ai/ha.

For synergistic control of selected weed species in sugar beet crops, the mixtures of the invention are best applied when the sugar beet plants are at about the cotyledon to two-leaf stage and the weed plants are correspondingly young. One skilled in the art can readily determine application rates and ratios of herbicide of Formula I to the herbicide of Formula II as well as timing necessary for the desired level of weed control and crop safety.

The Formula I sulfonylurea (Compound 1) was tested in combination with the mono isopropylamine salt of N-(phosphonomethyl)glycine (Formula II) (Compound 2).

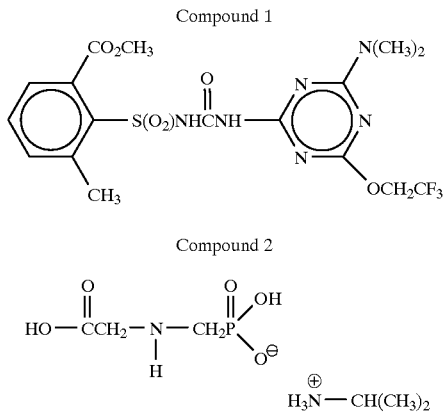

The following protocol was used for the test whose results are listed in Table 1. The data demonstrate the surprising efficacy of the Formula I and Formula II mixtures of this invention against specific weeds. The weed control afforded by the mixtures of this invention are not limited, however, to these species.

Test Protocol

Sugar beet crops were planted during the summer in an area of France having high natural infestations of weed species such as *Amaranthus retroflexus* (redroot pigweed) (AMARE), *Chenopodium album* (common lambsquarters) (CHEAL), and *Polygonum persicaria* (ladysthumb) (POLPE). Test plots were treated postemergence to the crops and weeds at the two-leaf stage of the sugar beet plants. Compound 1 was formulated as a single active ingredient in 50% strength dry flowable granules. Compound 2 was formulated as a high-surfactant aqueous solution containing the equivalent of 120 g/L of glyphosate acid (Formula II). Herbicides were applied to the test area by diluting the formulated herbicides in an aqueous solution to the appropriate concentration to deliver the desired use rate; spray volumes of about 150 L/ha were typically used. The prepared test solutions were then sprayed onto the test plots through standard T-Jet flat-fan nozzles. When applied as mixtures, Compounds 1 and 2 were tank mixed. No additional adjuvants such as surfactants were added to the spray solution. Individual treatments were replicated three times at the field trial location.

Assessments of weed control were made by visual inspection about 21 days following herbicide application. A visual rating system was used based on a percentage scale from 0 to 100%, relative to an adjacent untreated control plot or test area. On this scale 0% represents no visual differences relative to an untreated control, 100% represents complete kill of the given crop or weed species.

Colby's equation was used to calculate the expected additive herbicidal effect of the mixtures of Compound 1 and Compound 2. Colby's equation (Colby, S. R. "Calculating Synergistic and Antagonistic Responses of Herbicide Combinations," *Weeds*, 15(1), pp 20–22 (1967)) calculates the expected additive effect of herbicidal mixtures, and for two active ingredients is of the form:

$$P_{a+b} = P_a + P_b - (P_a P_b / 100)$$

wherein $P_{a+b}$ is the percentage effect of the mixture expected from additive contribution of the individual components, $P_a$ is the observed percentage effect of the first active ingredient at the same use rate as in the mixture, and $P_b$ is the observed percentage effect of the second active ingredient at the same use rate as in the mixture.

Table 1 represents visual assessments of control of specific weeds with Compound 1 and Compound 2 applied alone as single active ingredients, applied as a mixture of the two active ingredients of Compound 1 and Compound 2, and the expected additive effect of the herbicidal mixture of Compound 1 and Compound 2 (Colby's equation). Different ratios of Compound 1 to Compound 2, and different formulation types, also provide useful weed control from the combination of the two herbicides.

TABLE 1*

Effect of Compound 1 and Compound 2 as Active Ingredients Alone and in Mixture

| CMPD 1 | CMPD 2 | | AMARE | CHEAL | POLPE |
|---|---|---|---|---|---|
| Alone | | | | | |
| 10 | 0 | Mean | 0 | 0 | 0 |
| 15 | 0 | Mean | 10 | 10 | 10 |
| 0 | 250 | Mean | 82 | 46 | 47 |
| 0 | 500 | Mean | 93 | 83 | 67 |
| 0 | 1000 | Mean | 99 | 88 | 82 |
| Mixtures | | | | | |
| 10 | 250 | Mean | 86 | 52 | 50 |
| | | Colby† | 82 | 46 | 47 |
| 10 | 500 | Mean | 96 | 85 | 82 |
| | | Colby | 93 | 83 | 67 |
| 10 | 1000 | Mean | 99 | 97 | 96 |
| | | Colby | 99 | 93 | 82 |
| 15 | 250 | Mean | 91 | 72 | 60 |
| | | Colby | 84 | 51 | 52 |
| 15 | 500 | Mean | 98 | 85 | 82 |
| | | Colby | 94 | 85 | 70 |
| 15 | 1000 | Mean | 100 | 98 | 98 |
| | | Colby | 99 | 94 | 84 |

*Application rates are expressed in g ai/ha. Application rates for Compound 2 are expressed in terms of equivalent glyphosate acid (Formula II). Data are reported as percent control.
†Colby, S. R. "Calculating Synergistic and Antagonistic Responses of Herbicide Combinations," *Weeds*, 15(1), pp 20–22 (1967).

What is claimed is:

1. A herbicidal mixture comprising synergistic herbicidally effective amounts of the compound of Formula I

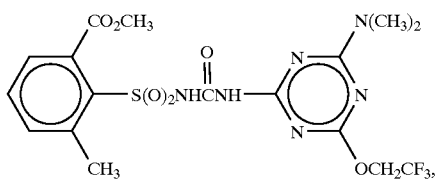

which is methyl 2-[[[[[4-(dimethylamino)-6-(2,2,2-trifluoroethoxy)-1,3,5-triazin-2-yl]amino]-carbonyl]amino]sulfonyl]-3-methylbenzoate (triflusulfuron methyl) and agriculturally suitable salts thereof
and the compound of Formula II

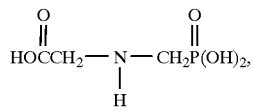

which is N-(phosphonomethyl)glycine (glyphosate) and agriculturally suitable salts thereof, wherein the compound of Formula I and the compound of Formula II are in a ratio by weight of from 1:15 to 1:100.

2. A mixture of claim 1 wherein the compound of Formula II is in the form of its mono isopropylamine salt.

3. A mixture of claim 1 wherein the compound of Formula II is in the form of its mono trimethylsulfonium salt.

4. An agriculturally suitable composition for controlling the growth of undesired vegetation comprising an effective amount of the herbicidal mixtures of claim 1 and at least one of the following: surfactant, solid or liquid diluent.

5. An agriculturally suitable composition for controlling the growth of undesired vegetation comprising an effective amount of the herbicidal mixtures of claim 2 and at least one of the following: surfactant, solid or liquid diluent.

6. An agriculturally suitable composition for controlling the growth of undesired vegetation comprising an effective amount of the herbicidal mixtures of claim 3 and at least one of the following: surfactant, solid or liquid diluent.

7. The composition of claim 4 wherein the undesired vegetation is the vegetation in a crop of sugar beet plants containing at least one gene that confers resistance to glyphosate and its agriculturally suitable salts.

8. A method for controlling the growth of undesired vegetation comprising contacting the locus to be protected with a herbicidally effective amount of the composition of claim 4.

9. A method for controlling the growth of undesired vegetation comprising contacting the locus to be protected with a herbicidally effective amount of the composition of claim 5.

10. A method for controlling the growth of undesired vegetation comprising contacting the locus to be protected with a herbicidally effective amount of the composition of claim 6.

11. The method of claim 8 wherein the locus to be protected is a crop of sugar beet plants containing at least one gene that confers resistance to glyphosate and its agriculturally suitable salts.

* * * * *